US012616970B2

(12) United States Patent (10) Patent No.: US 12,616,970 B2
Emaminejad et al. (45) Date of Patent: May 5, 2026

(54) DEVICE AND METHOD FOR NONINVASIVELY AND ELECTROCHEMICALLY SENSING IN VIVO BIOCHEMICALS

(71) Applicant: THE REGENTS OF THE UNIVERSITY OF CALIFORNIA, Oakland, CA (US)

(72) Inventors: Sam Emaminejad, Los Angeles, CA (US); Yichao Zhao, Los Angeles, CA (US); Bo Wang, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1074 days.

(21) Appl. No.: 17/763,149

(22) PCT Filed: Sep. 25, 2020

(86) PCT No.: PCT/US2020/052752
§ 371 (c)(1),
(2) Date: Mar. 23, 2022

(87) PCT Pub. No.: WO2021/062174
PCT Pub. Date: Apr. 1, 2021

(65) Prior Publication Data
US 2022/0387991 A1 Dec. 8, 2022

Related U.S. Application Data

(60) Provisional application No. 62/906,259, filed on Sep. 26, 2019.

(51) Int. Cl.
B01L 3/00 (2006.01)
A61B 5/145 (2006.01)
A61B 5/1468 (2006.01)

(52) U.S. Cl.
CPC ........ B01L 3/5027 (2013.01); A61B 5/14507 (2013.01); A61B 5/1468 (2013.01); B01L 2300/047 (2013.01); B01L 2300/0645 (2013.01)

(58) Field of Classification Search
CPC ............ B01L 3/5027; B01L 2300/047; B01L 2300/0645; A61B 5/14507; A61B 5/1468
See application file for complete search history.

(56) References Cited

U.S. PATENT DOCUMENTS

2002/0049389 A1* 4/2002 Abreu .................. A61B 3/0058
600/318
2004/0087671 A1* 5/2004 Tamada ................... C08J 3/075
516/99

(Continued)

FOREIGN PATENT DOCUMENTS

WO WO-2019/090161 A1 5/2019

OTHER PUBLICATIONS

Haison, Lin, A rapid and low -cost fabrication and integration scheme to render 3D microfluidic architectures for wearable biofluid sampling, manipulation and sensing, 2019, Royal Society of Chemistry. pp. 1-10. (Year: 2019).*

(Continued)

*Primary Examiner* — Charles Capozzi
*Assistant Examiner* — Alex Ramirez
(74) *Attorney, Agent, or Firm* — Foley & Lardner LLP

(57) ABSTRACT

Example implementations include a method of manufacturing a biochemical sensor by forming a fluid conduit in a microfluidic layer, forming an electrode on an electrode layer, forming a biochemical sensor on the electrode layer, bonding the electrode layer to a first surface of the microfluidic layer, and bonding a barrier layer to a second surface of the microfluidic layer. Example implementations also (Continued)

include a method of electrically detecting a biochemical by contacting an electrode array to a biological surface, obtaining a biofluid at the electrode array from the biological surface, obtaining a response current associated with the biofluid at the electrode array, and generating a quantitative biochemical response based at least partially on the response current. Example implementations further include applying a current to the biological surface. Example implementations further include filtering electrical interference at the electrode array. Example implementations further include generating a quantitative biochemical response based on the response current.

8 Claims, 11 Drawing Sheets

(56)                    References Cited

U.S. PATENT DOCUMENTS

| | | |
|---|---|---|
| 2010/0175821 A1 | 7/2010 | Cho et al. |
| 2018/0070869 A1 | 3/2018 | Ionescu et al. |
| 2019/0110722 A1 | 4/2019 | Ionescu et al. |
| 2019/0239778 A1 | 8/2019 | Srinivasan et al. |

OTHER PUBLICATIONS

Examination Report on European Application No. 20869056.0 date Oct. 2, 2024.

Examination Report on European Application No. 20869056.0 dated Mar. 13, 2025 (5 pages).

Amay J. Bandodkar et al.,(Battery-Free, Skin-Interfaced Microfluidic/ Electronic Systems for Simultaneous Electrochemical, Colorimetric, and Volumetric Analysis of Sweat)Science Advances, Jan. 18, 2019, pp. 1-15.

Foreign Action other than Search Report on PCT PCT/US2020/ 052752 dtd Nov. 30, 2020.

Foreign Search Report on PCT PCT/US2020/052752 dtd Feb. 9, 2021.

Haisong Lin et al.,(A Rapid and Low-Cost Fabrication and Integration Scheme to Render 3D Microfluidic Architectures for Wearable Biofluid Sampling, Manipulation, and Sensingt)Lab on a Chip; Jul. 18, 2019, pp. 12.

Yichao Zhao et al.,(A Wearable Freestanding Electrochemical Sensing System)Science Advances, Mar. 20, 2020, pp. 1-12.

Extended Search Report on European Application No. 20869056.0 dated Jan. 3, 2024.

* cited by examiner

100A

104A

140

110

130

102A

110

120

100B

104B

140

110

102B

110

120

400A

Form Fluid Conduit in Microfluidic Layer    410

Etch Sensor Chamber(s) into Microfluidic Layer    412

Etch Channel(s) into Microfluidic Layer    414

Etch Opening(s) into Microfluidic Layer    416

Etch Opening(s) into Barrier Layer    420

Form Electrode(s) on Electrode Layer    430

Form Grid Mask Matching Chamber(s)    432

Deposit Working Electrode Material    434

440

400C

Form Fluid Conduit in Microfluidic Layer

410C

Form Electrode on Electrode Layer

430C

Form Biochemical Sensor on Electrode Layer

450C

Bond Electrode Layer to Microfluidic Layer

460C

Bond Barrier Layer to Microfluidic Layer

462C

Figure 5A:
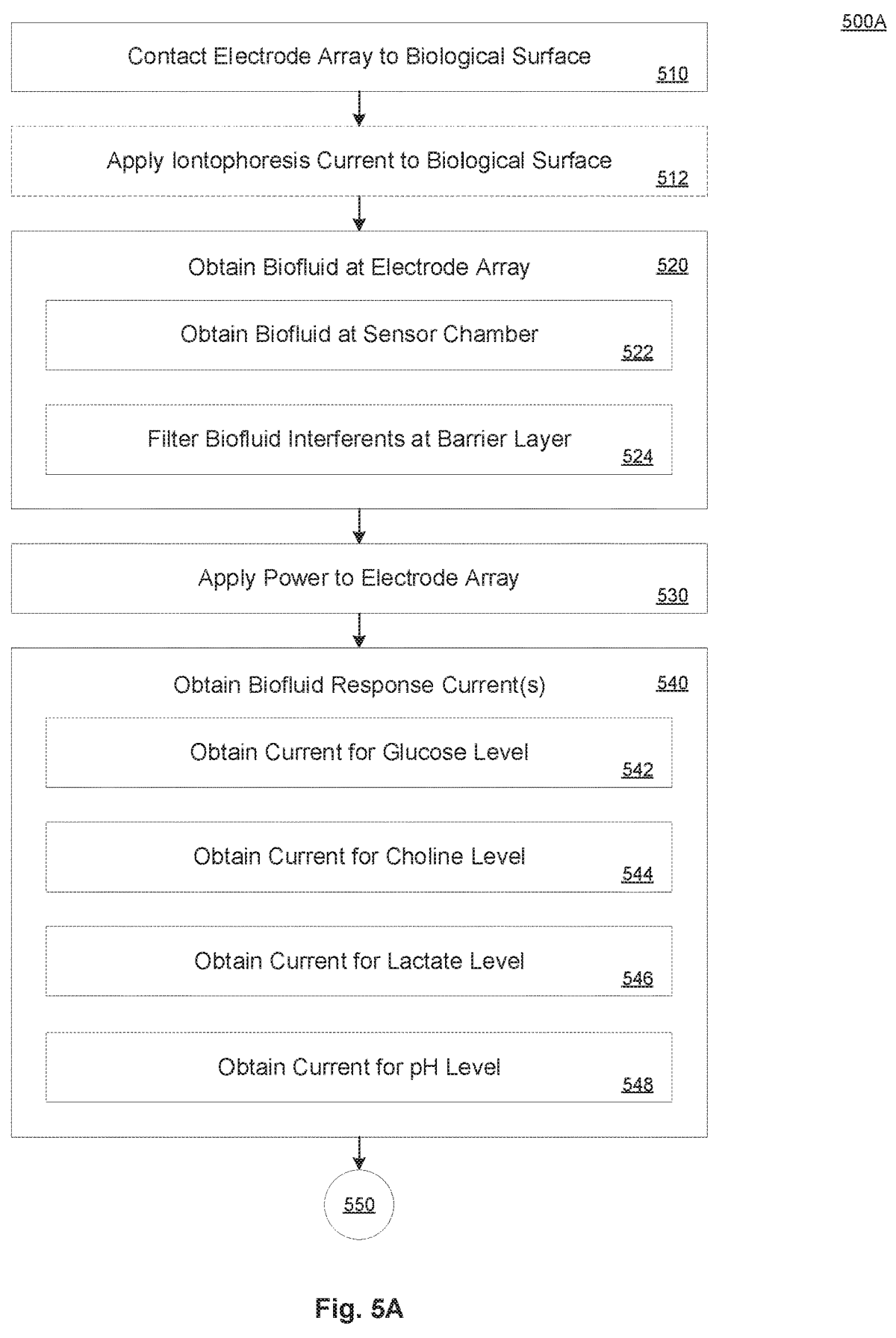

500A

```
┌─────────────────────────────────────────────────────────┐
│         Contact Electrode Array to Biological Surface     │
│                                                    510    │
└─────────────────────────────────────────────────────────┘
                            │
                            ▼
┌─────────────────────────────────────────────────────────┐
│       Apply Iontophoresis Current to Biological Surface   │
│                                                    512    │
└─────────────────────────────────────────────────────────┘
                            │
                            ▼
┌─────────────────────────────────────────────────────────┐
│         Obtain Biofluid at Electrode Array         520    │
│   ┌───────────────────────────────────────────────────┐  │
│   │        Obtain Biofluid at Sensor Chamber          │  │
│   │                                            522    │  │
│   └───────────────────────────────────────────────────┘  │
│   ┌───────────────────────────────────────────────────┐  │
│   │      Filter Biofluid Interferents at Barrier Layer│  │
│   │                                            524    │  │
│   └───────────────────────────────────────────────────┘  │
└─────────────────────────────────────────────────────────┘
                            │
                            ▼
┌─────────────────────────────────────────────────────────┐
│             Apply Power to Electrode Array         530    │
└─────────────────────────────────────────────────────────┘
                            │
                            ▼
┌─────────────────────────────────────────────────────────┐
│         Obtain Biofluid Response Current(s)        540    │
│   ┌───────────────────────────────────────────────────┐  │
│   │        Obtain Current for Glucose Level           │  │
│   │                                            542    │  │
│   └───────────────────────────────────────────────────┘  │
│   ┌───────────────────────────────────────────────────┐  │
│   │        Obtain Current for Choline Level           │  │
│   │                                            544    │  │
│   └───────────────────────────────────────────────────┘  │
│   ┌───────────────────────────────────────────────────┐  │
│   │        Obtain Current for Lactate Level           │  │
│   │                                            546    │  │
│   └───────────────────────────────────────────────────┘  │
│   ┌───────────────────────────────────────────────────┐  │
│   │          Obtain Current for pH Level              │  │
│   │                                            548    │  │
│   └───────────────────────────────────────────────────┘  │
└─────────────────────────────────────────────────────────┘
                            │
                            ▼
                          ( 550 )
```

DEVICE AND METHOD FOR NONINVASIVELY AND ELECTROCHEMICALLY SENSING IN VIVO BIOCHEMICALS

CROSS-REFERENCE TO RELATED PATENT APPLICATIONS

This application is a 371 National Stage Entry of International Application No. PCT/US2020/052752, filed Sep. 25, 2020, which claims the domestic benefit under Title 35 of the United States Code § 119(e) of U.S. Provisional Patent Application Ser. No. 62/906,259, entitled "Wearable Freestanding Electrochemical Sensing System," filed Sep. 26, 2019, the contents of such application being hereby incorporated by reference in its entirety and for all purposes as if completely and fully set forth herein.

FEDERALLY SPONSORED RESEARCH OR DEVELOPMENT

This invention was made with government support under Grant Number 1722972, awarded by the National Science Foundation. The government has certain rights in the invention.

TECHNICAL FIELD

The present implementations relate generally to biochemical sensing, and more particularly to noninvasively and electrochemically sensing in vivo biochemicals.

BACKGROUND

Health monitoring is increasingly desired to perform increasingly accurate health diagnostics and guide improved health outcomes for increasing numbers of users and activity scenarios. In particular, detection of biochemical levels of biofluids secreted by a user can provide significant health data and, in turn, drive significantly improved health outcomes. However, conventional systems may not effectively detect and isolate biochemicals in biofluids at in vivo sites noninvasively and accurately. In addition, conventional systems may not detect and isolate biochemicals in health-critical biofluids in vivo at sufficient speed to provide effective health modeling and guidance. Thus, a technological solution for noninvasively and electrochemically sensing in vivo biochemicals is desired.

SUMMARY

Example implementations include a method of manufacturing a biochemical sensor by forming a fluid conduit in a microfluidic layer, forming an electrode on an electrode layer, forming a biochemical sensor on the electrode layer, bonding the electrode layer to a first surface of the microfluidic layer, and bonding a barrier layer to a second surface of the microfluidic layer.

Example implementations also include a method of electrically detecting a biochemical by contacting an electrode array to a biological surface, obtaining a biofluid at the electrode array from the biological surface, obtaining a response current associated with the biofluid at the electrode array, and generating a quantitative biochemical response based at least partially on the response current. Example implementations further include applying a current to the biological surface. Example implementations further include filtering electrical interference at the electrode array. Example implementations further include generating a quantitative biochemical response based on the response current.

Example implementations also include a device with an electrode layer, a conductor disposed on the electrode layer, an analyte sensor layer disposed on the conductor and electrically responsive to a biochemical, and a microfluidic layer disposed on the electrode layer and comprising a sensor chamber region disposed at least partially surrounding the conductor. Example implementations further include a barrier layer disposed on a surface of the microfluidic layer opposite to the electrode layer.

BRIEF DESCRIPTION OF THE DRAWINGS

These and other aspects and features of the present implementations will become apparent to those ordinarily skilled in the art upon review of the following description of specific implementations in conjunction with the accompanying figures, wherein:

FIG. 5A illustrates an example method of electrically sensing a biochemical in accordance with present implementations.

DETAILED DESCRIPTION

Figure 1A:
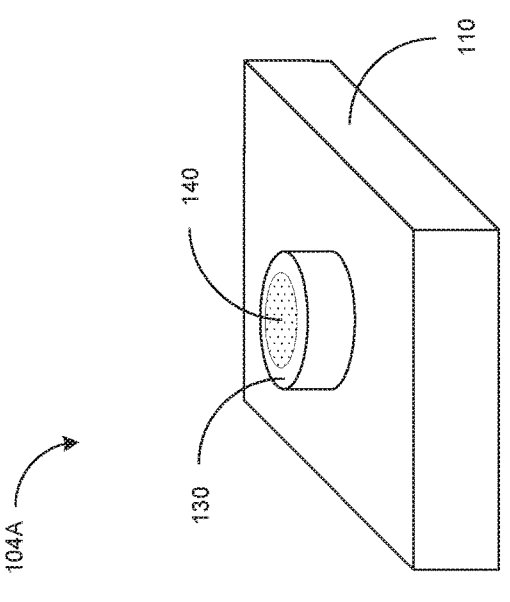
FIG. 1A illustrates an example device in accordance with present implementations.
Figure 1A:
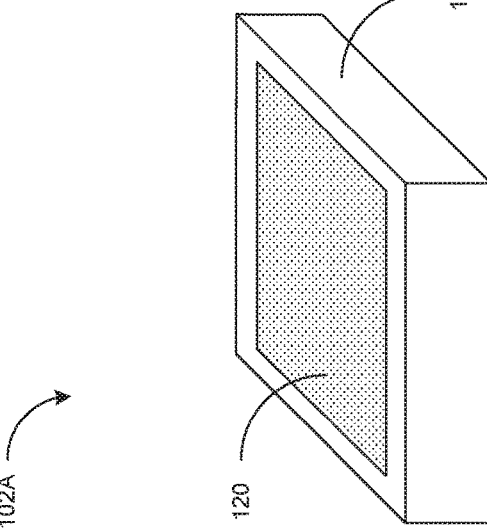

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of interchange of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

It is advantageous to provide a biochemical sensor array to provide a noninvasive electrochemical sensor effectively operable in a wide variety of use cases. it is further advantageous to provide a biochemical sensor array in a configuration including a plurality of stacked layers to minimize torque, stress, shear force, and the like applied to the sensor in response to movement, pressure, acceleration or the like by a user conducting an activity while wearing the biochemical sensor array. It is further advantageous to provide a biochemical sensor array in a configuration including a plurality of flexible layers to minimize torque, stress, shear force, and the like applied to the sensor in response to movement, pressure, acceleration or the like by a user conducting an activity while wearing the biochemical sensor array. As one example, a user wearing a biochemical sensor array on a limb may apply significant forces to the biochemical sensor array thereon during the course of strenuous activity in which biofluid is released. As one example, strenuous activity can include sweat-inducing exercise, exertion, and the like. As another example, strenuous activity can include running, boxing, cycling, and the like.

FIG. 1A illustrates a top view 102A and a bottom view 104A of an example device 100A in accordance with present implementations. As illustrated by way of example in FIG. 1, the example device 100A includes a housing 110, a display device 120, a stimulation module 130, and an electrochemical sensor 140.

The housing 110 contains or the like one or more sensors, electrical devices, electronic devices, mechanical structures, and the like. In some implementations, the housing 110 includes a plastic material, a polymer material, electrically insulating material, waterproof material, water resistant material, or the like. In some implementations, the housing 110 includes a 3D-printed structure. In some implementations, the housing 110 includes a first face oriented or orientable toward a biological surface. In some implementations, the housing 110 includes a second face oriented or orientable away from the biological surface. In some implementations, the first face and the second face of the housing 110 are disposed on opposite surfaces of the housing 110.

The display device 120 is operable to display one or more biochemical characteristics associated with a biofluid. In some implementations, the biofluid includes one or more characteristics associated with a biochemical therein. In some implementations, the biofluid includes one or more of glucose, choline, and lactate. In some implementations, the characteristics include a pH characteristic. In some implementations, the display device 120 includes an electronic display. In some implementations, the electronic display includes a liquid crystal display (LCD), a light-emitting diode (LED) display, an organic light-emitting diode (OLED) display, or the like. In some implementations, the display device 120 is housed at least partially within the housing 120, on its second face oriented or orientable away from the biological surface.

The stimulation module 130 is operable to apply electrical energy to the biological surface according to one or more electrical output patterns. In some implementations, the stimulation module 130 is operable to apply electrical energy to the biological surface in accordance with an iontophoresis process. In some implementations, the stimulation module 130 is operable to induce a biological reaction from the biological surface. In some implementations, a biological reaction includes release of biofluid from the biological surface. As one example, the stimulation module 130 can apply electrical energy to skin to induce release of sweat. In some implementations, the stimulation module 130 includes one or more electrical, electronic, and logical devices. In some implementations, the stimulation module 130 includes one or more integrated circuits, transistors, transistor arrays, or the like.

The electrochemical sensor 140 is operable to detect one or more biochemicals in contact therewith or contactable therewith. In some implementations, the electrochemical sensor 140 is operable to detect a plurality of biochemical. In some implementations, the electrochemical sensor 140 includes one or more electrode with biochemically-sensitive electrode terminals. In some implementations, the electrochemical sensor 140 includes a plurality of electrodes arranged in a geometric pattern. As one example, the plurality of electrodes can be arranged in a grid pattern including an arbitrary number of electrodes in a length direction and a width direction perpendicular to the length direction. In some implementations, the electrochemical sensor 140 include at least one opening, chamber, or the like, to receive biofluid from the biological surface and to contactably couple the biofluid to at least one electrode terminal, biochemically-sensitive electrode terminal, or a combination thereof. In some implementations, the biochemical sensor 140 includes one or more polymers, plastics, or the like. In some implementations, the biochemical sensor 140 includes one or more films, sheets, layers, or the like. In some implementations, the biochemical sensor 140 is or includes one or more films, sheets, layers, or the like arranged in a planar structure. In some implementations, the biochemical sensor 140 is or includes a flexible structure deformable, bendable, or the like in one or more planar directions.

Figure 1B:
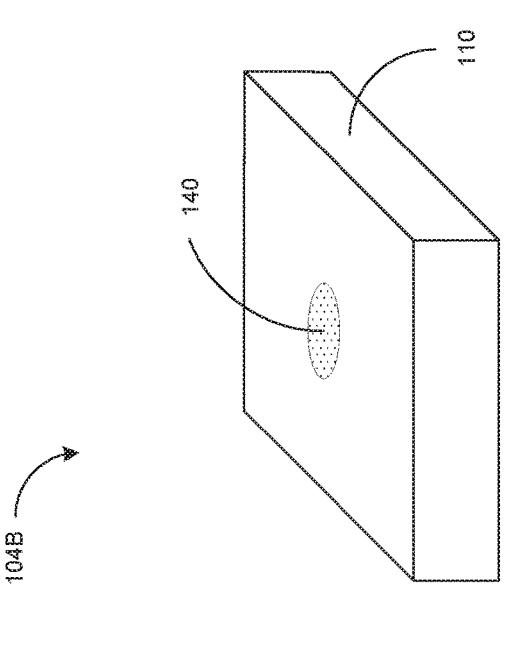
FIG. 1B illustrates a further example device in accordance with present implementations.
Figure 1B:
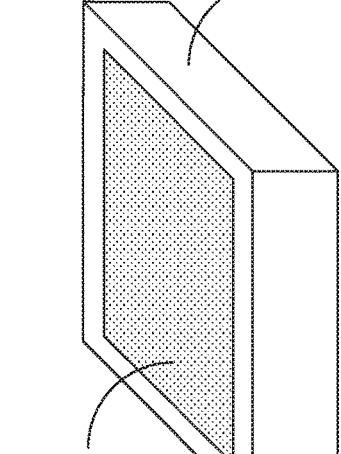

FIG. 1B illustrates a top view 102B and a bottom view 104B of a further example device 100B in accordance with present implementations. As illustrated by way of example in FIG. 2, the example device 100B includes the housing 110, the display device 120, and the electrochemical sensor 140. In some implementations, the example device 100B includes the housing 110 and the display device 120 correspondingly to those of the example device 100A. In some implementations, the example device 100B does not include the stimulation module 130, and the electrochemical sensor 140 is disposed on, over, in, or the like, the housing 110.

Figure 2A:
FIG. 2A illustrates a cross-sectional view of an example electrochemical sensor further to the example devices of FIGS. 1A and 1B.

FIG. 2A illustrates a cross-sectional view 200A of an example electrochemical sensor 140 further to the example devices of FIGS. 1A and 1B. As illustrated by way of example in FIG. 2A, an example electrochemical sensor 140 includes an electrode layer 210, an electrode material 212, a biochemical sensor material 214, a microfluidic layer 220, a fluid chamber 222, a fluid channel 224, a barrier layer 230, and an adhesive layer 240. In some implementations, the electrochemical sensor 140 is coupled to, integrated with, integrable with, or the like, the housing 110 and any components therein. In some implementations, the electrochemical sensor 140 is indirectly coupled to the housing 110 by the stimulation module. Alternatively, in some implementations, the electrochemical sensor 140 is directly coupled to the housing 110, where the housing includes the stimulation module 130. Alternatively, in some implementations, the electrochemical sensor 140 is directly coupled to the housing 110, where the housing does not include the stimulation module 130. In some implementations, the electrochemical sensor is contactable with a biological surface 250 of a biological object 252.

The electrode layer 210 includes a planar surface having at least one electrode formed thereon. In some implementations, the electrode layer 210 includes an adhesive conductive film bonding or operable to bond the electrode layer 210 to the housing 110. In some implementations, the electrode layer 210 has a first planar surface having one or more electrodes patterned, deposited, or the like, thereon. In some implementations, the electrode layer 210 includes a second surface opposite to the first planar surface and in direct or indirect contact with the housing 110. Alternatively, in some implementations, the electrode layer 210 includes a second surface opposite to the first planar surface and in direct or indirect contact with the stimulation module 130. In some implementations, the electrode layer 210 is or includes an anisotropic conductive film (ACF). In some implementations, the electrode layer 210 is operatively coupled to one or more electrical, electronic, or like components housed at least partially within the housing 110. In some implementations, the electrode layer 210 has a thickness of approximately 50 micrometers in a depth direction perpendicular to a plane thereof. In some implementations, the electrode layer 210 is directly operatively coupled to one or more of the electrical, electronic, or like components of the housing 110 by a conductive characteristic thereof. As one example, an electrical conductivity characteristic of the electrode layer 210 can permit transmission of electrical current, voltage, signal, or the like between an electrode disposed on a first surface of the electrode layer 210 and an electrical or electronic component in contact with a second opposite surface of the electrode layer 210. In some implementations, individual electrodes of a plurality fabricated on the electrode layer 210 are disposed at a predetermined distance from each other to minimize or eliminate electrical interference from differing electrical current, voltage, signal, or the like traveling perpendicularly through the plane of the electrode layer 210 and associated with different electrodes disposed on the electrode layer 210.

The electrode material 212 includes at least one metallic portion forming at least part of at least one electrode terminal, biochemically-sensitive electrode terminal, or a combination thereof. In some implementations, the electrode material 212 is disposed on a first planar surface of the electrode layer 210 in one or more electrically isolated, electrically disconnected, or like configurations. In some implementations, the electrode material 212 is disposed in a grid pattern on the electrode layer 210. In some implementations, the electrode material 210 is or includes one or more noble metal electrode array films. As one example, the electrode material can include gold (Au), platinum (Pt), or the like, or a combination thereof. As another example, the electrode material can include nanoparticles including gold (Au), platinum (Pt), or the like, or a combination thereof. In some implementations, the electrode material 212 is in direct contact with the electrode layer 210. Thus, in some implementations, the combination of an ACF conductive electrode layer and noble metal electrode material eliminate the need for a metallic adhesive layer. As one example, a metallic adhesive layer can include one or more of chromium or titanium.

The biochemical sensor material 214 includes at least one sensor responsive to at least one chemical, biochemical, or the like. In some implementations, the biochemical sensor material 214 is disposed on a first planar surface of the electrode layer 210 in one or more electrically isolated, electrically disconnected, or like configurations. In some implementations, the biochemical sensor material 214 is disposed in a grid pattern on the electrode layer 210. In some implementations, the biochemical sensor material 214 is disposed in a grid pattern directly on the electrode material 212. In some implementations, the biochemical sensor material 214 includes glucose oxidase and is electrically responsive to contact with glucose. In some implementations, the biochemical sensor material 214 includes choline oxidase and is electrically responsive to contact with choline. In some implementations, the biochemical sensor material 214 includes lactate oxidase and is electrically responsive to contact with lactate. In some implementations, the biochemical sensor material 214 includes iridium oxide and is electrically responsive to pH level of a fluid in contact therewith.

The microfluidic layer 220 includes at least one cavity in at least one structure operable to capture fluid. In some implementations, the cavity of the microfluidic structure 220 includes at least one opening in a planar structure thereof. In some implementations, the microfluidic layer 220 is or includes a flexible planar structure. As one example, the microfluidic structure can be a flexible plastic film. As another example, the microfluidic structure can be a flexible plastic adhesive tape. In some implementations, the microfluidic structure 220 has a thickness of approximately 170 micrometers in a depth direction perpendicular to a plane thereof. In some implementations, the microfluidic layer 220 is an adhesive tape layer disposed between the electrode layer 210 and the barrier layer 230. In some implementations, the adhesive layer is or includes a double-sided adhesive tape layer. In some implementations, the microfluidic layer 220 is bonded to the first surface of the electrode layer 210 including at least one of the electrode material 212 and the biochemical sensor material 214.

In some implementations, the microfluidic layer 220 includes at least one fluid chamber 222. In some implementations, the cavity of the microfluidic structure 220 includes at least one fluid chamber 222 formed in a planar structure thereof. In some implementations, the fluid chamber 222 is one of a plurality of fluid chambers disposed within the microfluidic layer 220. In some implementations, the fluid chamber 222 is one of a plurality of fluid chambers disposed in a grid pattern correspondingly to a grid pattern of the electrode material 212 on the electrode layer 210. In some implementations, the fluid chamber 222 is aligned with at least one electrode including at least the electrode material 212. Thus, in some implementations, the fluid chamber at least partially encloses an electrode including at least the electrode material 212 and disposed on the electrode layer 210. In some implementations, the microfluidic layer 220 includes at least one fluid channel 224. In some implementations, the cavity of the microfluidic structure 220 includes at least one fluid channel 224 formed in a planar structure thereof. In some implementations, the fluid channel 224 is one of a plurality of fluid channels disposed within the microfluidic layer 220. In some implementations, the fluid channel 224 is one of a plurality of fluid channels connecting a plurality of fluid chambers disposed in a grid pattern correspondingly to a grid pattern of the electrode material 212 on the electrode layer 210.

The barrier layer 230 includes a planar structure bonded to the microfluidic layer 220. In some implementations, the barrier layer 230 has a first planar surface having one or more cavities, openings, or the like formed therein and bonded to the microfluidic structure 220. In some implementations, the cavities, openings or the like, of the barrier layer allow fluid to enter the fluid chamber 222 from a biological surface. In some implementations, the barrier layer 230 includes a second surface opposite to the first planar surface and in direct or indirect contact with the biological surface. Alternatively, in some implementations, the barrier layer 230 includes a second surface opposite to the first planar surface and in direct or indirect contact with the adhesive layer 240. In some implementations, the barrier layer 230 has a thickness of approximately 100 micrometers in a depth direction perpendicular to a plane thereof. In some implementations, the barrier layer 230 is or includes polyethylene terephthalate (PET) or the like. Thus, in some implementations, microfluidic channels are chambers are cavities bounded in a direction by the electrode layer 210, bounded on one or more sides by the microfluidic layer 220, and bounded below the barrier layer 230 as a floor. The adhesive layer 240 includes a planar structure bonded or bondable to the barrier layer 230, and bonded or bondable to the biological surface. In some implementations, the adhesive layer 240 is or includes a double-sided adhesive tape layer. It is to be understood that the adhesive layer is optionally included in the electrochemical sensor 140.

Figure 2B:
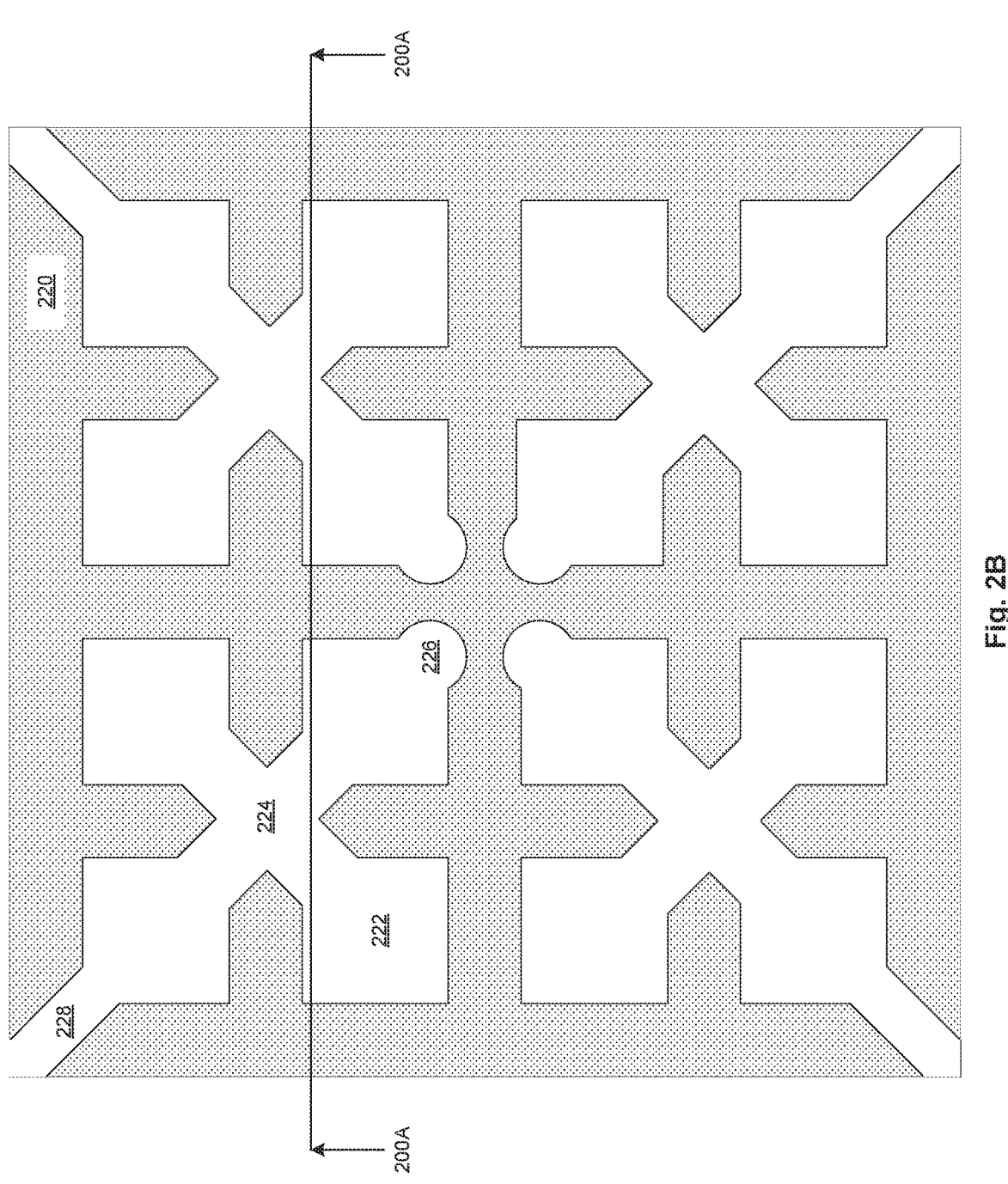
FIG. 2B illustrates a plan view of an example microfluidic layer further to the example electrochemical sensor of FIG. 2A.

FIG. 2B illustrates a plan view 200B of the example microfluidic layer 220 further to the example electrochemical sensor 140 of FIG. 2A. As illustrated by way of example in FIG. 2B, the example microfluidic layer 220 includes multiple fluid chambers 222, multiple fluid channels 224, multiple fluid inlets 226, and multiple fluid outlets 228. The fluid chambers 222, the fluid channels 224, the fluid inlets 226, and the fluid outlets 228 are cavities formed by removing one or more portions of the microfluidic layer 220.

In some implementations, the fluid chambers are arranged in one or more grid patterns corresponding to one or more grid patterns for electrodes including at least the electrode material 212. In some implementations, the fluid chambers 222 extend through the depth of the microfluidic layer. In some implementations, the fluid chambers have a planar area of 12 mm². In some implementations, the fluid channels 224 are arranged to connect at least two fluid chambers 222. In some implementations, the fluid channels 224 are arranged to connect at least one fluid chamber 222 of the plurality to at least one fluid inlet 226 of the plurality. In some implementations, the fluid channels 224 are arranged to connect at least one fluid chamber 222 of the plurality to at least one fluid outlet 228 of the plurality. In some implementations, the fluid channels 224 are arranged in overlapping or intersecting pathways. Alternatively, in some implementations, the fluid channels 224 are arranged in one pathway sequentially, serially, or the like, connecting at least a subset of the fluid chambers 222. As one example, the fluid channels 224 can be arranged in a circle, loop, spiral, or like pathway. In some implementations, the fluid channels 224 connect a plurality of fluid chambers into independent and distinct fluid pathways between fluid inlets and fluid outlets. As one example, the fluid channels 224 can connect the fluid chambers 222 into four distinct fluid pathways, groups, or the like, as illustrated in FIG. 2B.

The fluid inlets 226 are operable to route fluid from a biological surface to one or more fluid chambers 222. In some implementations, one or more fluid inlets 226 align with one or more cavities, openings, or the like, in the barrier layer 230. Thus, in some implementations, biofluid from a biological surface travels into an opening of the barrier layer in contact with the biological surface. Further, in some implementations, the biofluid travels from the opening of the barrier layer 230 into the microfluidic structure 220 by at least one fluid inlet 226. In some implementations, the fluid outlets 228 are operable to expel fluid from one or more fluid chambers 222 of the microfluidic chamber 220 from the microfluidic chamber 220. In some implementations, the fluid outlets 228 are disposed or sandwiched between the electrode layer 210 and the barrier layer 230, allowing biofluid from the fluid chambers to drain from the electrochemical sensor 140. In some implementations, biofluid from the fluid chambers drains from the electrochemical sensor 140 by a dripping, cascading, or like process by the fluid outlets 228. In some implementations, biofluid from the fluid chambers drains from one or more sides of the electrochemical sensor 140 perpendicular to the planar surface thereof by the fluid outlets 228.

Figure 3:
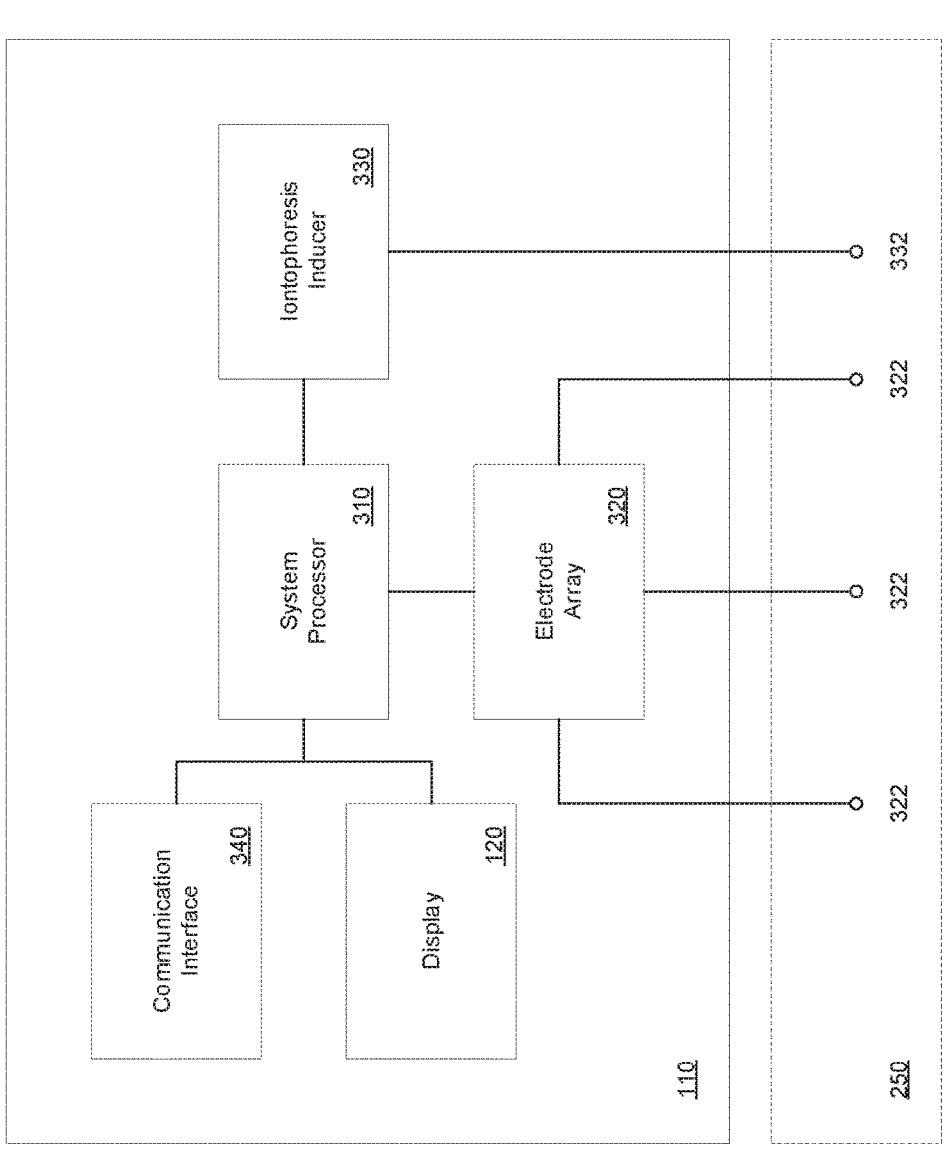
FIG. 3 illustrates an example electronic sensor device in accordance with present implementations.

FIG. 3 illustrates an example electronic sensor device in accordance with present implementations. As illustrated by way of example in FIG. 3, an example electronic sensor device 300 includes a system processor 310, an electrode array 320, a biosensor electrode terminal 322, an iontophoresis inducer 330, an iontophoresis electrode terminal 332, a communication interface 340, and the display device 120. In some implementations, the example electronic sensor device 300 is housed at least partially within the housing 110. In some implementations, the electronic sensor device 300, including but not limited to the biosensor electrode terminal 322 and the iontophoresis electrode terminal 332, is contactable with a biological surface 250.

The system processor 310 is operable to execute one or more instructions associated with input from the electrochemical sensor 140. In some implementations, the system processor 310 is an electronic processor, an integrated circuit, or the like including one or more of digital logic, analog logic, digital sensors, analog sensors, communication buses, volatile memory, nonvolatile memory, and the like. In some implementations, the system processor 310 includes but is not limited to, at least one microcontroller unit (MCU), microprocessor unit (MPU), central processing unit (CPU), graphics processing unit (GPU), physics processing unit (PPU), embedded controller (EC), or the like. In some implementations, the system processor 310 includes a memory operable to store or storing one or more instructions for operating components of the system processor 310 and operating components operably coupled to the system processor 310. In some implementations, the one or more instructions include at least one of firmware, software, hardware, operating systems, embedded operating systems, and the like. It is to be understood that the system processor 310 or the device 300 generally can include at least one communication bus controller to effect communication between the system processor 310 and the other elements of the device 300.

The electrode array 320 is operable to detect electrical responses from one or more of the biosensor electrode terminals 322 and to communicate the electrical responses to the system processor. In some implementations, the electrode array 320 includes a power source, battery, power controller, potentiostat, or the like, operable to apply or maintain a working voltage at one or more of the biosensor electrode terminals 322. In some implementations, the working voltage is a voltage of +0.5 V. In some implementations, the electrode array 320 includes one or more analog signal processors, transformers, or the like, operable to convert one or more received response currents from one or more of the biosensor electrode terminals 332 to one or more corresponding response voltages or the like. As one example, the electrode array 320 can convert a response current associated with a particular biochemical response to a response voltage having a magnitude corresponding to the biochemical response. In some implementations, the electrode array includes a low pass filter or the like operable to minimize motion-inducted noise in the electrical response current received from one or more of the biosensor electrode terminals. In some implementations, the low pass filter operates at or approximately at 1 Hz.

In some implementations, the electrode array 320 includes one or more logical or electronic devices including but not limited to integrated circuits, logic gates, flip flops, gate arrays, programmable gate arrays, and the like. In some implementations, the electrode array 320 includes the electrochemical sensor 140. It is to be understood that any electrical, electronic, or like devices, or components associated with the electrode array can also be associated with, integrated with, integrable with, replaced by, supplemented by, complemented by, or the like, the system processor 310 or any component thereof. The biosensor electrode terminal 322 is operable to operatively couple the electrode array 320 to the biological surface 250. In some implementations, the biosensor electrode terminal 322 includes one or more of the electrode layer 210, the electrode material 212, and the biochemical sensor material 214 associated with, contained within, partially surrounded by, or the like, a corresponding fluid chamber 222. In some implementations, a single biosensor electrode terminal 322 corresponds to a single electrode of the electrochemical sensor 140. In some implementations, the electrochemical sensor 140 includes a plurality of biosensor electrode terminals 322. In some implementations, the electrochemical sensor 140 includes a plurality of biosensor electrode terminals 322 arranged in a grid or like configuration.

The iontophoresis inducer 330 is operable to control, generate, define, or the like, one or more signals, pulses, or the like, of electrical energy applied to the biological surface according to one or more electrical output patterns. In some implementations, the iontophoresis inducer 330 is operable to apply electrical energy to the biological surface in accordance with an iontophoresis process. In some implementations, the stimulation module 130 includes the iontophoresis inducer 330. In some implementations, the iontophoresis inducer 330 is operable to induce a biological reaction from the biological surface in accordance with the operation of the stimulation module 130. In some implementations, the iontophoresis inducer 330 includes one or more electrical, electronic, and logical devices. In some implementations, the iontophoresis inducer 330 includes one or more integrated circuits, transistors, transistor arrays, or the like. The iontophoresis electrode terminal 332 is operable to apply one or more signals, pulses, or the like, of electrical energy to the biological surface according to one or more electrical output patterns in response to signals, instructions, or the like received from the iontophoresis inducer 330. In some implementations, the stimulation module 130 includes the iontophoresis electrode terminal 332. In some implementations, the iontophoresis electrode terminal include at least one conductive electrode material, and a conductive lead, wire, connector, or the like.

The communication interface 340 is operable to communicatively couple at least the system processor 310 to at least one external device. In some implementations, the communication interface 114 includes one or more wired interface devices, channels, and the like. In some implementations, the communication interface includes, is operably coupled to, or is operably couplable to an I2C, UART, or like communication interface by one or more external devices, systems, or the like. In some implementations, the communication interface includes a network or an Internet communication interface or is operably couplable to an Internet communication interface by one or more external devices, systems, or the like. The display device 120 is operable to visually communicate one or more electrical responses received at the electrode array 130. In some implementations, the display device is operably coupled to at least the system processor 310.

Figure 4A:
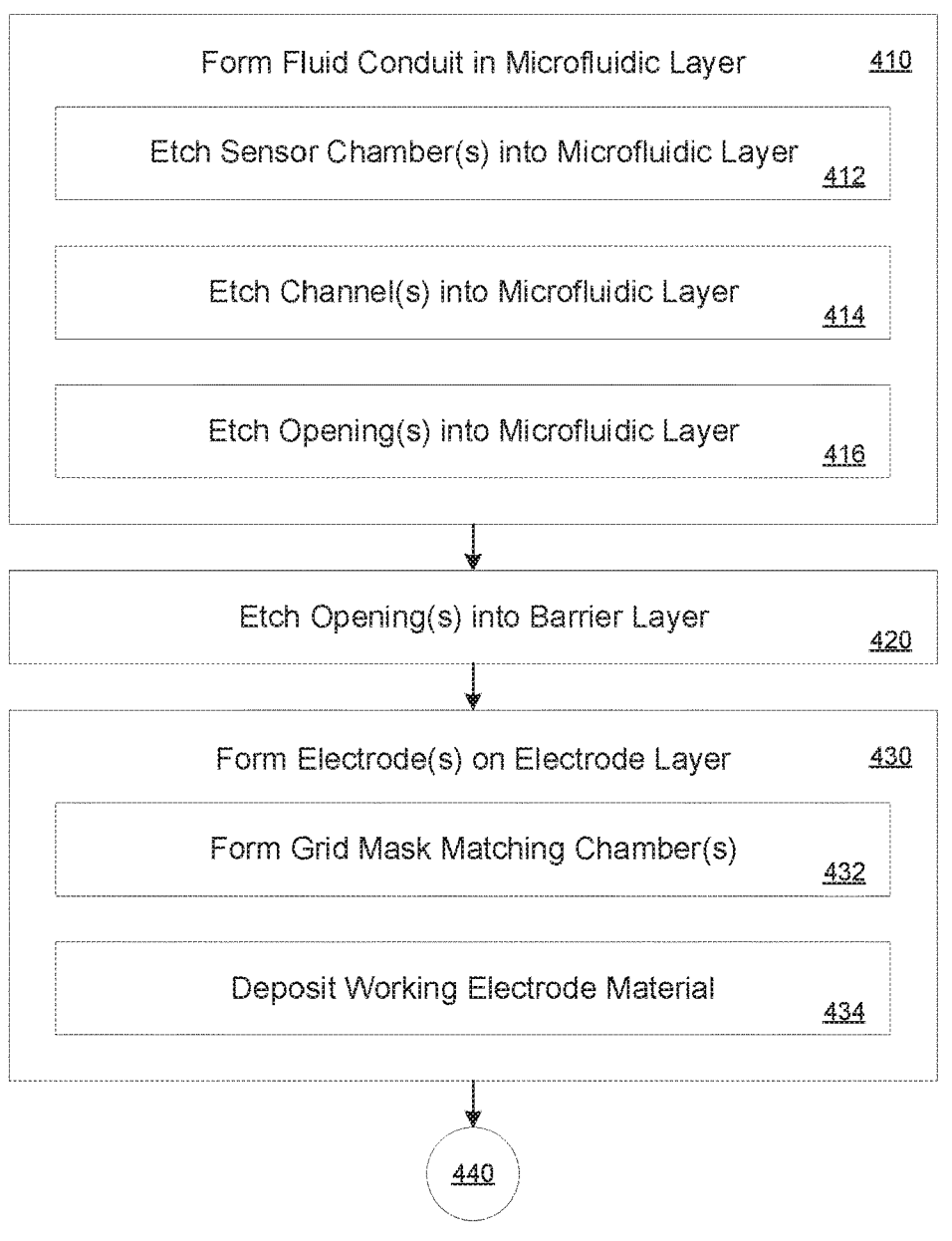
FIG. 4A illustrates an example method of manufacturing an example electrochemical sensor in accordance with present implementations.

FIG. 4A illustrates an example method of manufacturing an example electrochemical sensor in accordance with present implementations. In some implementations, at least one of the example device 100A and 100B is formed by method 400A according to present implementations. In some implementations, the method 400A begins at step 410.

At step 410, the example system forms a fluid conduit in a microfluidic layer. In some implementations, the example system forms the fluid conduit by removing at least a portion of the microfluidic layer 220. In some implementations, the example system removes one or more portions of the microfluidic layer 220 by forming at least one opening, cavity, or the like, in a depth direction of the microfluidic layer 220 perpendicular to a plane thereof. In some implementations, the example system removes all material within a predetermined region of the microfluidic layer 220. In some implementations, the example system forms at least one of the fluid chamber 222, the fluid channel 224, the fluid inlet 226 and the fluid outlet 228 in accordance with at least one pattern, mask or the like. In some implementations, the example system forms at least one commonly connected network including at least one of the fluid chamber 222, the fluid channel 224, the fluid inlet 226 and the fluid outlet 228 in accordance with at least one pattern, mask or the like.

In some implementations, step 410 includes at least one of steps 412, 414 and 416. At step 412, the example system etches a sensor chamber into the microfluidic layer. In some implementations, the example system removes a portion of the microfluidic layer by etching a sensor chamber into the microfluidic chamber 220. In some implementations, the etching includes etching by one or more lasers in a cutting or like action. In some implementations, the sensor chamber corresponds to at least one fluid chamber 222. At step 414, the example system etches a channel into the microfluidic layer. In some implementations, the example system forms at least one fluid channel 224 into the microfluidic layer 220 correspondingly to step 412. At step 416, the example system etches an opening into the microfluidic layer. In some implementations, the example system for at least one fluid inlet 226 in the microfluidic layer 220 correspondingly to step 412. In some implementations, the example system for at least one fluid outlet 228 in the microfluidic layer 220 correspondingly to step 412. The method 400A then continues to step 420.

At step 420, the example system etches an opening into a barrier layer. In some implementations, the example system etches the opening into the barrier layer 230 by removing at least a portion of the barrier layer 230. In some implementations, the example system removes one or more portions of the barrier layer 230 by forming at least one opening, cavity, or the like, in a depth direction of the barrier layer 230 perpendicular to a plane thereof. In some implementations, the example system removes one or more portions of the barrier layer 230 correspondingly to step 410. In some implementations, the example system removes all material within a predetermined region of the barrier layer 230. In some implementations, the example system forms at least one opening into the barrier layer 230 in alignment with or corresponding to the fluid outlet 228. In some implementations, the example system forms at least one opening into the barrier layer 230 in alignment with or corresponding to the fluid outlet 228 in accordance with at least one pattern, mask or the like barrier layer 130 corresponding to at least one pattern, mask or the like of the microfluidic layer 220. The method 400A then continues to step 430.

At step 430, the example system forms an electrode on an electrode layer. In some implementations, step 430 includes at least one of steps 432 and 434. At step 432, the example system forms a grid mask corresponding to at least one sensor chamber associated with the microfluidic layer. In some implementations, the grid mask is or includes a patterned layer including one or more openings therein to allow deposition of electrode material directly on designated portions of the electrode layer 210. In some implementations, the patterned layer includes one or more grid patterns. In some implementations, the patterned layer includes one or more grid patterns corresponding to an arrangement of one or more fluid chambers 222 as illustrated in FIG. 2B. At step 434, the example system deposits electrode material on the electrode layer. In some implementations, the electrode material includes one or more of gold (Au) and platinum nanoparticles (PtNP). In some implementations, the exemplary system deposits a 200 nm thick layer of Au onto the electrode layer. In some implementations, the example system then deposits PtNP over the Au layer by chemical reduction in an aqueous solution of 2.5 mM $H_2PtCl_6$ and 1.5 mM formic acid. As one example, a chemical reduction process includes applied voltage of −0.1 V vs. Ag/AgCl, and a reduction period of 10 min. In some implementations, the method 400A then continues to step 440.

Figure 4B:
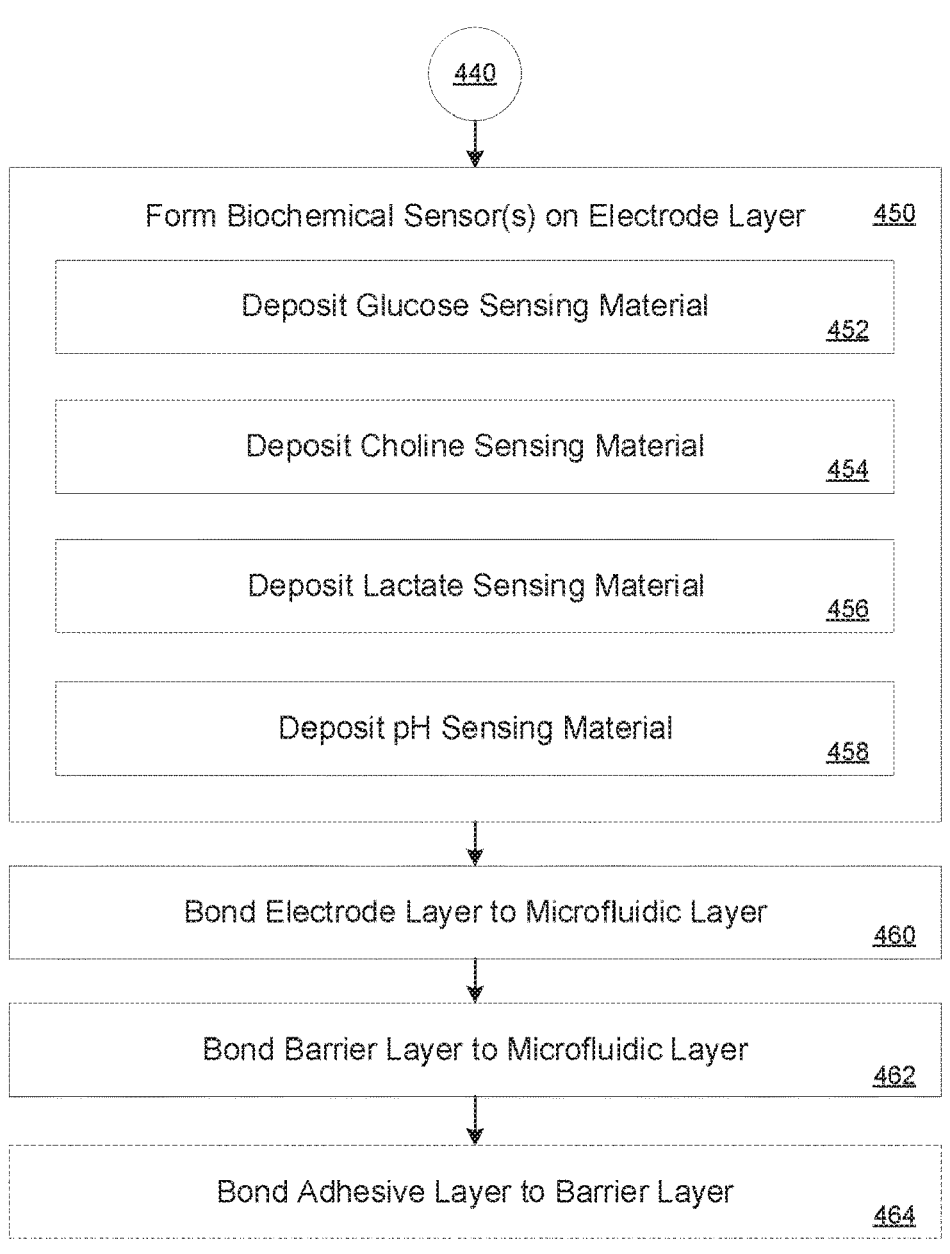
FIG. 4B illustrates an example method of manufacturing an example electrochemical sensor further to the example method of FIG. 4A.

FIG. 4B illustrates an example method of manufacturing an example electrochemical sensor further to the example method of FIG. 4A. In some implementations, at least one of the example device 100A and 100B is formed by method 400B according to present implementations. In some implementations, the method 400B begins at step 440. The method 400B then continues to step 450.

At step 450, the example system forms a biochemical sensor on the electrode layer. In some implementations, the example system deposits a poly-m-phenylenediamine (PPD) layer on the electrode formed in step 430. In some implementations, the example system deposits the PPD electrochemically by applying a 0.85 V (vs. Ag/AgCl) voltage for 300 s in PBS solution. In some implementations, the electrodes are then washed with deionized water or the like. In some implementations, the example system forms a chitosan solution incorporated in one or more processes or forming one or more types of biochemical sensors on the electrode array. In some implementations, the chitosan solution is a 1% chitosan solution. In some implementations, the 1% chitosan solution is formed by dissolving chitosan in a 2% acetic acid solution, including heating the solution including the chitosan to 60° C. for 30 minutes until the chitosan is fully dissolved. In some implementations, a reference electrode is formed by capping one or more electrodes with a reference electrode material. In some implementations, the reference electrode material includes silver (Ag) or silver chloride (AgCl) ink. In some implementations, forming the reference electrode includes heating an electrode having Ag/AgCl ink deposited thereon to a temperature of 80° C. for 10 min. In some implementations, step 450 includes at least one of steps 452, 454, 456 and 458.

At step 452, the example system deposits a glucose sensing material on the electrode layer. In some implementations, the glucose sensing material includes the 1% chitosan solution and a glucose oxidase solution. In some implementations, the glucose sensing material is deposited on at least one electrode. In some implementations, the resulting solution is formed, maintained, or the like, at a pH of 7.2 or substantially neutral. In some implementations, the resulting solution is formed with equal or substantially equal parts 1% chitosan solution and glucose oxidase solution.

At step 454, the example system deposits a choline sensing material on at least one electrode. In some implementations, the example system deposits choline oxidase on at least one electrode. In some implementations, the example system subsequently dries the deposited choline oxidase solution, and deposits the 1% chitosan solution on the dried choline oxide solution. In some implementations, the example system deposits 0.5 microliters of choline oxidase per electrode formed.

At step 456, the example system deposits a lactate sensing material on the electrode layer. In some implementations, the example system deposits a lactate oxidase solution on at least one electrode. In some implementations, the example system subsequently dries the deposited lactate oxidase solution, and deposits the 1% chitosan solution on the dried lactate oxide solution. In some implementations, the example system subsequently deposits a 3% PVC solution on the dried lactate oxidase solution. At step 458, the example system deposits a pH sensing material on the electrode layer. In some implementations, the pH sensing material is or includes iridium oxide. In some implementations, the depositing the pH sensing material includes an electrodeposition process for the iridium oxide. The method 400B then continues to step 460.

At step 460, the example system bonds the electrode layer to the microfluidic layer. In some implementations, at least one of the electrode layer 210 and the microfluidic layer 220 includes an adhesive material disposed on at least one planar surface thereof. In some implementations, the electrode layer 210 is bonded to the microfluidic layer 220 with the electrodes of the electrode layer 210 in alignment with the fluid chambers 222 of the microfluidic layer 220 in one or more planar directions of both layers 210 and 220. In some implementations, a planar surface of the electrode layer 210 on which the electrode are formed is bonded to a planar surface of the microfluidic layer 220. Thus, in some implementations, the bonding of the electrode layer 210 and the microfluidic layer 220 results in the formation of at least one electrode chamber having an electrode at least partially surrounded at its sides by walls of the fluid chambers 222. The method 400B then continues to step 462.

At step 462, the example system bonds the barrier layer to the microfluidic layer. In some implementations, at least one of the barrier layer 230 and the microfluidic layer 220 includes an adhesive material disposed on at least one planar surface thereof. In some implementations, the barrier layer 230 is bonded to the microfluidic layer 220 with the openings of the barrier layer 230 in alignment with the fluid inlets 226 of the microfluidic layer 220 in one or more planar directions of both layers 210 and 220. Thus, in some implementations, the bonding of the barrier layer 230 and the microfluidic layer 220 results in the formation of at least one electrode chamber having an electrode at least partially enclosed at its sides by walls of the fluid chambers 222 and at a side opposite to the electrode by the barrier layer 230. The method 400B then continues to step 464.

At step 464, the example system bonds the adhesive layer to the barrier layer. In some implementations, that adhesive layer includes at least one material compatible with temporarily, compatibly, or the like, bonding with the biological surface 250. It is to be understood that the example system can optionally bond the adhesive layer 240 to the barrier layer 230, or optionally include the adhesive layer 240 in the electrochemical sensor 140. In some implementations, the method 400B ends at step 464.

Figure 4C:
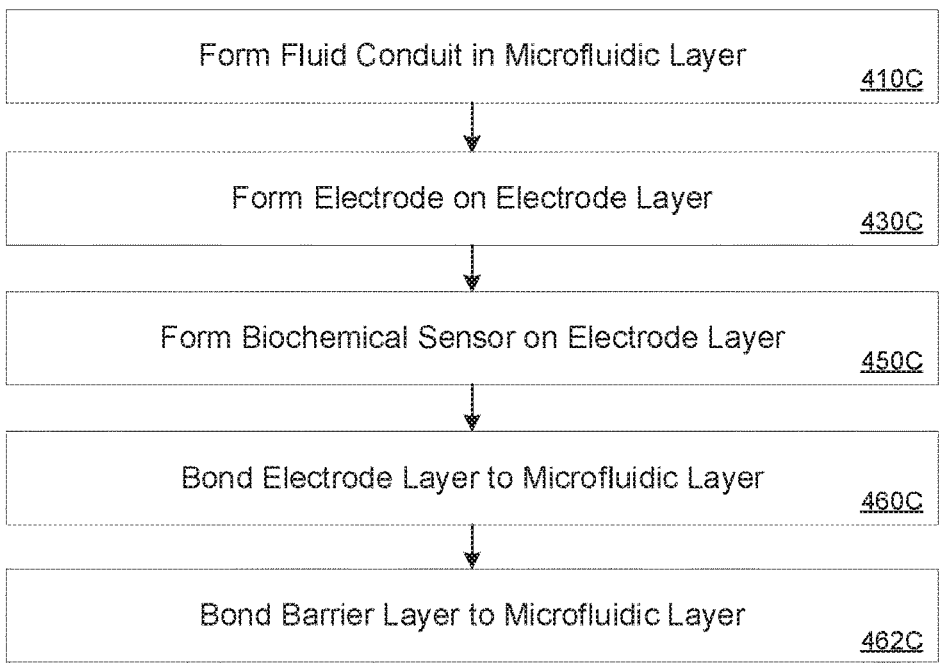
FIG. 4C illustrates a further example method of manufacturing an example electrochemical sensor in accordance with present implementations.

FIG. 4C illustrates a further example method of manufacturing an example electrochemical sensor in accordance with present implementations. In some implementations, at least one of the example device 100A and 100B is formed by method 400C according to present implementations. In some implementations, the method 400C begins at step 410C. At step 410C, the example system forms a fluid conduit in a microfluidic layer. In some implementations, step 410C at least partially corresponds to step 410. The method 400C then continues to step 430C. At step 430C, the example system forms an electrode on the electrode layer. In some implementations, step 430C at least partially corresponds to step 430. The method 400C then continues to step 450C. At step 450C, the example system forms a biochemical sensor on the electrode layer. In some implementations, step 450C at least partially corresponds to step 450. The method 400C then continues to step 460C. At step 460C, the example system bonds the electrode layer to the microfluidic layer. In some implementations, step 460C at least partially corresponds to step 460. The method 400C then continues to step 462C. At step 462C, the example system bonds the barrier layer to the microfluidic layer. In some implementations, step 462C at least partially corresponds to step 462. In some implementations, the method 400C ends at step 462C.

FIG. 5A illustrates an example method of electrically sensing a biochemical in accordance with present implementations. In some implementations, at least one of the example device 100A and 100B performs method 500A according to present implementations. In some implementations, the method 500A begins at step 510.

At step 510, the example system contacts an electrode array to a biological surface. In some implementations, the example system contacts the electrode array 130 to the biological surface 250 by the adhesive layer 240. The method 500A then continues to step 512.

At step 512, the example system applies an iontophoresis current to the biological surface. It is to be understood that the example system can optionally apply the iontophoresis current. It is to be understood that the example system can optionally apply the iontophoresis current based on control of one or more of the system processor 310, the iontophoresis inducer 330, the communication interface 340, and the stimulation module 130. In some implementations, the applied iontophoresis current increase an amount or rate of secretion of a biofluid from the biological surface 250. In some implementations, the iontophoresis current is applied constantly or according to a predetermined pattern to induce sweat or to induce a particular amount or rate of sweat secretion from the biological surface 250. The method 500A then continues to step 520.

At step 520, the example system obtains a biofluid at the electrode array. In some implementations, the biofluid secreted from the biological surface 250 travels into the electrode array by one or more of the microfluidic layer 220, and the barrier layer 230. In some implementations, the biofluid travels into an opening of the barrier layer 230 from the biological surface 250, then into a fluid inlet 226 from the opening of the barrier layer 230. In some implementations, step 520 includes at least one of steps 522 and 524. At step 522, the example system obtains the biofluid at a sensor chamber. In some implementations, the biofluid travels into the fluid chamber 222, either directly or by one or more intervening fluid channels 224 and fluid chambers 222. At step 524, the example system filters a biofluid interferent at a barrier layer 230. It is to be understood that in some implementations, the example system can additionally or alternatively filter interferents at the electrode layer 220. As one example, interferents include glucose, lactate, creatinine, choline, potassium chloride, sodium chloride, pilocarpine, aspirin, metformin, and albumin. The method 500A then continues to step 530.

At step 530, the example system applies power to the electrode array. In some implementations, the example system applies a constant 0.5 V current to electrodes of the electrode array, including biochemically responsive and reference biosensor electrode terminals 332. In some implementations, the example system applies the iontophoresis current to the biological surface 250 by the iontophoresis electrode terminal 332 concurrently with applying power to the electrode terminal 332 of the electrode array. The method 500A then continues to step 540.

At step 540, the example system obtains a biofluid response current. In some implementations, step 540 includes at least one of steps 542, 544, 546 and 548. At step 542, the example system obtains a response current associated with a glucose level at the electrode array. In some implementations, a glucose response current ranges from 0.0 microamps to 2.0 microamps for glucose concentrations ranging from 0.0 mM to 1.0 mM. At step 544, the example system obtains a response current associated with a choline level at the electrode array. In some implementations, a choline response current ranges from 0.0 microamps to 0.3 microamps for choline concentrations ranging from 0.0 mM to 0.4 mM. At step 546, the example system obtains a response current associated with a lactate level at the electrode array. In some implementations, a lactate response current ranges from 0.0 microamps to 1.8 microamps for lactate concentrations ranging from 0.0 mM to 15.0 mM. At step 548, the example system obtains a response current associated with a pH level at the electrode array. In some implementations, a pH response current ranges from 0.0 microamps to 5.0 microamps for hydrogen peroxide concentrations ranging from 0.0 mM to 0.2 mM. In some implementations, the method 500A then continues to step 550.

Figure 5B:
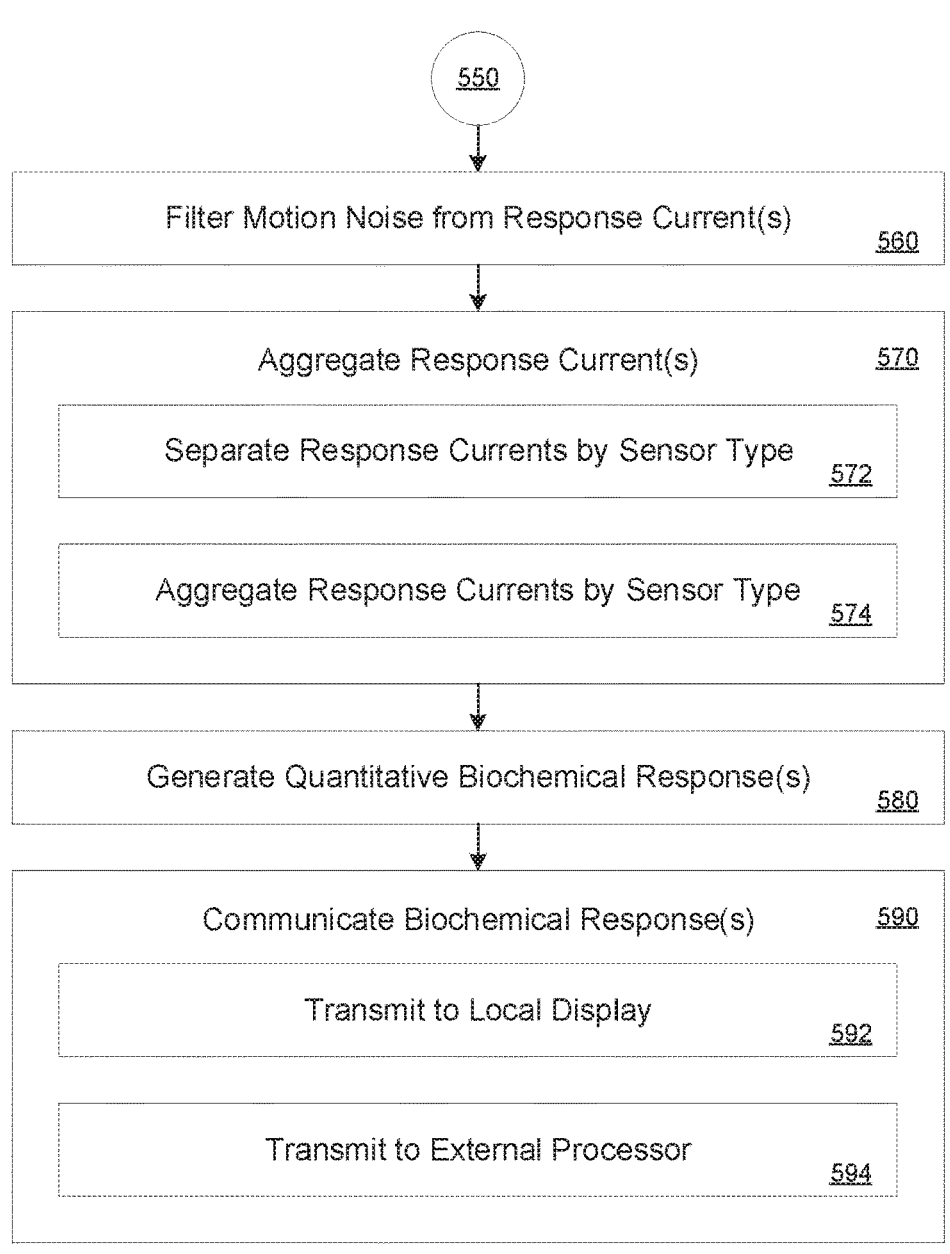
FIG. 5B illustrates an example method of electrically sensing a biochemical further to the example method of FIG. 5A.

FIG. 5B illustrates an example method of electrically sensing a biochemical further to the example method of FIG. 5A. In some implementations, at least one of the example device 100A and 100B performs method 500B according to present implementations. In some implementations, the method 500B begins at step 550. The method 500B then continues to step 560.

At step 560, the example system filters motion noise from the response current. In some implementations, the system processor 310 filters motion noise from the response current. In some implementations, motion noise includes variations of a response current generated in response to physical movement of an electrode array relative to a biological surface. As one example, physical movement can include shaking, shifting, jostling, shaking, vibrating, or the like of a housing including a sensor device. In some implementations, physical movement of the housing 110 is generated in response to physical movement of a wearer of a device including the electrode array 320. In some implementations, the example system filters the motion noise by passing the response current through a low pass filter to remove one or more high frequency artifacts from the response current. The method 500B then continues to step 570.

At step 570, the example system aggregates one or more response currents. In some implementations, the example system receives multiple response currents associated with a common biochemical sensor. As one example, an electrode array can include multiple glucose sensors, and each glucose sensor can provide its own corresponding glucose response current. In some implementations, step 570 includes at least one of steps 572 and 574. At step 572, the example system separate response currents by sensor type. In some implementations, the example system can identify a response current associated with a particular response. As one example, the system processor can be configured to associated certain electrodes at certain predetermined array indices with their physical parameters. As another example, the system processor 310 can be configured to identify all glucose or like sensors based on the location of each glucose sensor in the array. At step 574, the example system aggregates response currents by sensor type. In some implementations, the system processor 310 can combine, aggregate, average, or the like, a plurality of response currents associated with a like biochemical response sensor. The aggregated response can, in some implementations, further reduce noise, variability, distortion, and the like, in the electrical response to the presence of a particular biochemical. The method 500B then continues to step 580. At step 580, the example system generates a quantitative biochemical response. In some implementations, the example system generates the quantitative biochemical response by converting an analog response current to a digital response. In some implementations, the system processor generates the quantitative biochemical response by an analog-to-digital converter therein or therewith. It is to be understood that the system can optionally generate the quantitative biochemical response subsequent to aggregating the response currents, where multiple response currents are obtained by the example system. The method 500B then continues to step 590.

At step 590, the example system communicates the biochemical response. In some implementations, step 590 includes at least one of steps 592 and 594. At step 592, the example system transmits the biochemical response to the local display. At step 594, the example system transmits the biochemical response to an external processor. In some implementations, the external processor includes a remote server, remote computer, remote database, and the like. In some implementations, the method 500B ends at step 590.

Figure 5C:
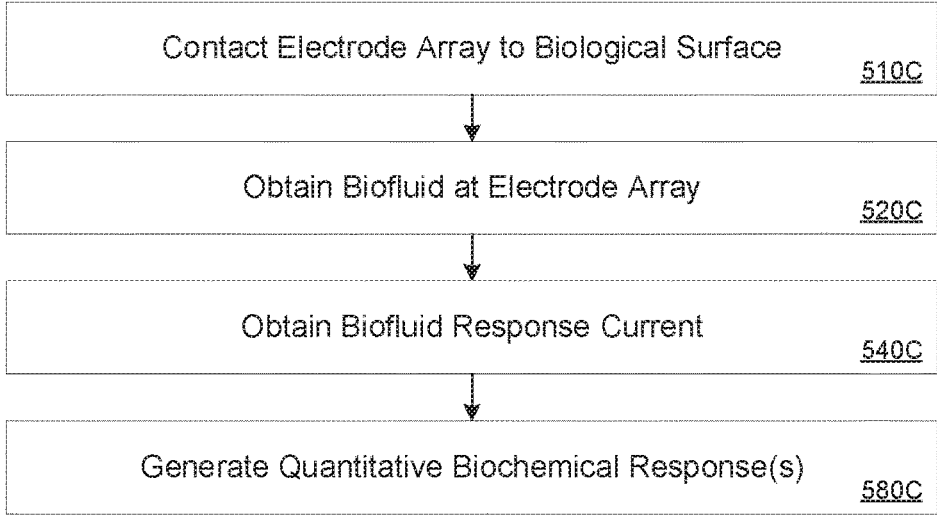
FIG. 5C illustrates a further example method of electrically sensing a biochemical in accordance with present implementations.

FIG. 5C illustrates a further example method of electrically sensing a biochemical in accordance with present implementations. In some implementations, at least one of the example device 100A and 100B performs method 500C according to present implementations. In some implementations, the method 500C begins at step 510C. At step 510C, the example system contacts an electrode array to a biological surface. In some implementations, step 510C at least partially corresponds to step 510. The method 500C then continues to step 520C. At step 520C, the example system obtains a biofluid at the electrode array. In some implementations, step 520C at least partially corresponds to step 520. The method 500C then continues to step 540C. At step 540C, the example system obtains a biofluid response current. In some implementations, step 540C at least partially corresponds to step 540. The method 500C then continues to step 580C. At step 580C, the example system generates a quantitative biochemical response. In some implementations, step 580C at least partially corresponds to step 580. In some implementations, the method 500C ends at step 580.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A method of electrically detecting a biochemical, the method comprising:
    contacting an electrode array to a biological surface, wherein the electrode array comprises a plurality of electrodes respectively associated with a plurality of biochemical sensors;
    obtaining a biofluid at the electrode array from the biological surface;
    obtaining a response current associated with the biofluid at the electrode array, wherein obtaining the response current includes aggregating a plurality of response currents from the plurality of biochemical sensors into an aggregated response current; and
    generating a quantitative biochemical response based at least partially on the aggregated response current.

2. The method of claim 1, further comprising:
    applying a current to the biological surface in accordance with at least one parameter corresponding to an iontophoresis process.

3. The method of claim 1, wherein the obtaining the biofluid further comprises obtaining the biofluid at a sensor chamber of a microfluidic layer adjacent to the electrode array.

4. The method of claim 1, further comprising:
    filtering an interferent at a barrier layer disposed between the electrode array and the biological surface.

5. The method of claim 1, further comprising:
    filtering electrical interference at the electrode array caused by motion of the biological surface at the electrode array.

6. The method of claim 1, wherein the obtaining the response current further comprises separating response currents associated with the biofluid a sensor type of the plurality of biochemical sensors from response currents not associated with the sensor type of the plurality of biochemical sensors.

7. The method of claim 1, wherein the biofluid comprises one or more of glucose, choline, and lactate.

8. The method of claim 7, wherein a magnitude of each of the plurality of the response currents corresponds to an amount of the glucose, the choline, or the lactate present in the biofluid, or a pH characteristic associated with the biofluid.

* * * * *